US011241283B2

(12) United States Patent
Hancock et al.

(10) Patent No.: US 11,241,283 B2
(45) Date of Patent: Feb. 8, 2022

(54) ELECTROSURGICAL INSTRUMENT FOR RADIATING MICROWAVE ENERGY AND DISPENSING LIQUID AT A TREATMENT SITE

(71) Applicant: CREO MEDICAL LIMITED, Chepstow (GB)

(72) Inventors: Christopher Paul Hancock, Bath (GB); Shaun Preston, Chepstow (GB); Zacharias P. Tsiamoulos, Canterbury (GB); Brian Saunders, Rickmansworth (GB)

(73) Assignee: CREO MEDICAL LIMITED, Chepstow (GB)

( * ) Notice: Subject to any disclaimer, the term of this patent is extended or adjusted under 35 U.S.C. 154(b) by 228 days.

(21) Appl. No.: 15/781,675

(22) PCT Filed: Dec. 7, 2016

(86) PCT No.: PCT/EP2016/080138
§ 371 (c)(1),
(2) Date: Jun. 5, 2018

(87) PCT Pub. No.: WO2017/097856
PCT Pub. Date: Jun. 15, 2017

(65) Prior Publication Data
US 2018/0296267 A1 Oct. 18, 2018

(30) Foreign Application Priority Data

Dec. 7, 2015 (GB) ...................................... 1521522

(51) Int. Cl.
*A61B 18/18* (2006.01)
*A61M 25/00* (2006.01)
(Continued)

(52) U.S. Cl.
CPC ...... *A61B 18/1815* (2013.01); *A61M 25/0084* (2013.01); *A61B 2018/00077* (2013.01);
(Continued)

(58) Field of Classification Search
CPC ........ A61B 18/1815; A61B 2018/1861; A61B 2018/1869; A61B 2018/1853;
(Continued)

(56) References Cited

U.S. PATENT DOCUMENTS 5,236,424 A * 8/1993 Imran ............... A61M 25/0074
604/264
5,298,682 A 3/1994 Salz
(Continued)

FOREIGN PATENT DOCUMENTS

CN 103329347 A 9/2013
EP 2 085 978 A2 8/2009
(Continued)

OTHER PUBLICATIONS

British Search Report of related British Patent Application No. GB1521522.1 dated May 10, 2016.
(Continued)

*Primary Examiner* — Shefali D Patel
*Assistant Examiner* — Avery Smale
(74) *Attorney, Agent, or Firm* — Arent Fox LLP (57) ABSTRACT

An electrosurgical device capable of both: (i) generating a radiative microwave field to perform either blood coagulation or sterilization, and (ii) dispensing a liquid to a target area, e.g. adrenaline for the treatment of peptic ulcers. Using microwave energy allows controlled coagulation which is unaffected by changes in tissue impedance during coagulation, and which can achieve a high level of coagulation within a given time. The electrosurgical device comprises a probe tip having a coaxial transmission line that includes a
(Continued)

hollow inner conductor having a dielectric material formed on an inner surface thereof. A liquid-conveying channel is located inside the dielectric material. The probe tip includes a conductive element coupled to receive microwave energy from the coaxial transmission line, the conductive element forming a radiating antenna structure for emitting a microwave EM field outwardly from the probe tip.

23 Claims, 10 Drawing Sheets

(51) Int. Cl.
*A61B 18/00* (2006.01)
*A61M 5/00* (2006.01)

(52) U.S. Cl.
CPC .............. *A61B 2018/00589* (2013.01); *A61B 2018/00755* (2013.01); *A61B 2018/1861* (2013.01); *A61B 2018/1892* (2013.01); *A61M 5/00* (2013.01)

(58) Field of Classification Search
CPC . A61B 2018/00077; A61B 2018/1892; A61M 2025/0089; A61M 25/0084; A61M 2025/0004; A61M 2025/0039; A61M 25/0045; A61M 25/0082; A61M 2025/0175; A61M 25/0606; A61M 25/065; A61M 2205/0233; A61M 2205/05; A61M 2205/368; A61M 2205/3686
See application file for complete search history.

(56) References Cited

U.S. PATENT DOCUMENTS

| | | | | |
|---|---|---|---|---|
| 5,403,311 | A | * | 4/1995 | Abele ................. A61B 18/1477 604/21 |
| 6,663,625 | B1 | * | 12/2003 | Ormsby ................. A61B 18/18 606/41 |
| 2009/0082762 | A1 | * | 3/2009 | Ormsby ............. A61B 18/1815 606/33 |
| 2009/0222002 | A1 | * | 9/2009 | Bonn ..................... A61B 18/18 606/33 |
| 2010/0004650 | A1 | | 1/2010 | Ormsby et al. |
| 2010/0168727 | A1 | * | 7/2010 | Hancock ............ A61B 18/1815 606/33 |
| 2010/0312054 | A1 | * | 12/2010 | Beyar ..................... A61B 1/04 600/108 |
| 2011/0213352 | A1 | | 9/2011 | Lee et al. |
| 2013/0281851 | A1 | | 10/2013 | Carr |
| 2014/0290830 | A1 | | 10/2014 | Brannan |
| 2015/0272673 | A1 | | 10/2015 | Cronin et al. |

FOREIGN PATENT DOCUMENTS

WO   WO 2009/039093 A2   3/2009
WO   WO-2012095653 A1 *   7/2012   ......... A61B 18/1815

OTHER PUBLICATIONS

International Search Report of related International Patent Application No. PCT/EP2016/080138 dated Feb. 13, 2017.
Written Opinion of related International Patent Application No. PCT/EP2016/080138 dated Feb. 13, 2017.
Communication from the State Intellectual Property Office of People's Republic of China in counterpart Application No. 201680072166.1, dated Apr. 30, 2020.

* cited by examiner

ELECTROSURGICAL INSTRUMENT FOR RADIATING MICROWAVE ENERGY AND DISPENSING LIQUID AT A TREATMENT SITE

CROSS-REFERENCE TO RELATED APPLICATIONS

This application is a National Stage Entry of International Patent Application No; PCT/EP2016/080138, filed Dec. 7, 2016, which claims priority to Great Britain Patent Application No. 1521522.1, filed Dec. 7, 2015. The disclosures of the priority applications are incorporated in their entirety herein by reference.

FIELD OF THE INVENTION

The invention relates to an electrosurgical instrument for the administration of a liquid to a target area within the body, and for emission of a microwave field, e.g. for vessel coagulation at the same target area. The invention also relates to an electrosurgical apparatus incorporating the electrosurgical instrument.

BACKGROUND TO THE INVENTION

It is known that microwave energy can be used to stem bleeds by causing coagulation of blood, e.g. in the gastrointestinal tract. It is also known that in the case of more serious, or larger-scale bleeds, it is desirable to administer liquid medicine such as adrenaline to the site of the bleed. Conventionally, in order to do this, it has been necessary to remove the microwave emitter from the body cavity experiencing the bleed, in order to inject adrenaline. This means that no microwave coagulation can occur for the entire period that the adrenaline is being injected, reducing the stemming of the blood flow.

SUMMARY OF THE INVENTION

At its most general, the present invention provides an electrosurgical device that is capable of both generating a radiative (i.e. non-ionizing) microwave field to perform coagulation of blood (or sterilization), and dispensing a liquid to a target area, e.g. adrenaline for the treatment of peptic ulcers. Herein, "microwave fields", "microwave radiation" and "microwave energy" or similar refer to electromagnetic radiation having a frequency of 400 MHz to 100 GHz, and more preferably 1 GHz to 60 GHz. Specific frequencies that have been considered are: 915 MHz, 2.45 GHz, 3.3 GHz, 5.8 GHz, 10 GHz, 14.5 GHz and 24 GHz. Using microwave energy allows controlled coagulation which is not limited by the effect of the impedance of the coagulated tissue, and which is able to achieve a high level of coagulation within a given time. The use of microwaves also presents a lower risk of injury due to burning than other techniques such as bipolar RF coagulation.

In order to achieve the dual functionality described above, the present invention may provide an electrosurgical instrument comprising: an elongate probe having: a coaxial transmission line for conveying microwave electromagnetic (EM) energy, a probe tip connected at the distal end of the coaxial transmission line for receiving the microwave energy, and a liquid channel located inside the coaxial transmission line for conveying liquid through the elongate probe to the probe tip, wherein the coaxial transmission line comprises: a hollow inner conductor, an outer conductor, a first dielectric material separating the inner conductor from the outer conductor, and a hollow second dielectric material on an inner surface of the hollow inner conductor, the liquid channel located inside the hollow second dielectric material; wherein the probe tip has a probe tip channel running therethrough, the probe tip channel terminating in an aperture at its distal end, and wherein the probe tip includes a conductive element coupled to receive microwave energy from the coaxial transmission line, the conductive element forming a radiating antenna structure for emitting a microwave EM field outwardly from the probe tip.

Herein, references to "conductive" and "conductor" means electrically conductive unless the context indicates otherwise.

The conductive element may be connected to at least one of the inner conductor and outer conductor to form the radiating antenna structure.

The probe tip may comprise a continuation of the hollow second dielectric material beyond a distal end of the coaxial transmission line. The probe tip channel may thus include or consist of a passageway defined by the continuation of the hollow second dielectric material. The distal end of the coaxial transmission line may be defined at the point where the outer conductor terminates. The hollow inner conductor may also extend into the probe tip, where it forms all or part of the conductive element.

The probe tip preferably comprises a tip body formed from a third dielectric material, the tip body being connected to the distal end of the coaxial transmission line. For example, the third dielectric material may be mounted over the continuation of the hollow second dielectric material. The probe tip channel may thus run through the third dielectric material. The third dielectric material may be the same as or different from the first dielectric material and/or the second dielectric material.

In one embodiment, the inner and outer conductors may be joined into a half-wavelength loop at the probe tip, whereby the emitted microwave EM field is an H field formed inside the loop.

In use, the probe tip is positioned at a treatment target area, e.g. the site of an internal bleed, or a peptic ulcer. The device is able to operate in two modes:

(i) microwave radiation mode: the radiating antenna structure emits non-ionising microwave radiation for vessel coagulation (ii) liquid delivery mode: liquid is provided from a liquid source to the liquid channel from which it may be dispensed into the target area. This mode may be effected by flooding the liquid channel with liquid.

The probe tip has a proximal end, connected to the distal end of the coaxial transmission line, and a distal end opposite to this, which may be in contact with the target area during use of the electrosurgical instrument. The probe tip channel joins the proximal end and the distal end of the probe tip. The aperture is located at the distal end of the probe tip channel. In use, the aperture provides access to a target area for liquid delivery.

A hollow, e.g. hypodermic needle may be provided inside the liquid channel, wherein a first end of the hollow needle is in fluid communication with the liquid channel and a second end of the hollow needle is arranged to deliver liquid from the liquid channel through the aperture of the probe tip channel to a target area. The second end of the needle is preferably located inside the probe tip channel, proximal to the aperture. In use, in a liquid delivery mode, liquid is provided from a liquid source to the liquid channel, from which it enters the first end of the needle, and flows along the needle, exiting at the second end of the needle into the probe tip channel and out of the aperture, or if the second end of the needle is located outside the probe tip channel.

The needle may be connected to the inner conductor, and be exposed at an odd number of quarter-wavelengths from the aperture, such that the needle is able to act as a radiating antenna structure.

Advantageously, the needle may be adjustable between a retracted position and an exposed position, wherein when the needle is in an exposed position, the second end of the needle is located external to the probe tip, i.e. in contact with, or closely adjacent to the target area, and when the needle is in the retracted position, the second end of the needle remains inside the probe tip. Alternatively, when the needle is in a retracted position, the second end of the needle may be retracted all the way back inside the coaxial transmission line to which the probe tip is connected. Retraction of the needle allows a user to ensure that the needle is not in an exposed position during emission of a microwave field by the radiating antenna structure.

In order to effect the adjustment of the needle between the exposed and retracted positions, the electrosurgical instrument may be provided with needle-adjustment means, for example a guide wire may be attached at or near the first end of the needle, the guide wire passing along the liquid channel, so that adjustment of the needle can be controlled from the proximal end of the liquid channel. This enables adjustment of the needle while the device is in use.

In order to prevent emission of a microwave field when the needle is in the exposed position, the inner conductor of the coaxial transmission line may have an axial gap, and the needle-adjustment means may include a conducting ring, arranged to bridge the gap in the inner conductor when the needle is in the retracted position. When the needle is in the exposed position, the conducting ring is arranged no longer to bridge the gap in the inner conductor, breaking the electrical connection, and thus power is not delivered to the probe tip, preventing emission of the microwave field.

Alternatively, a sensor may be used to detect whether or not the needle is located in the exposed position. Possible sensors include a return loss sensor, a proximity detector, or a photodetector. When such a sensor detects that the needle is in the exposed position, it may prevent operation of the device in microwave radiation mode.

A needle feed tube may also be attached to the first end of the needle to supply the needle with a liquid to be administered to a target area. In this way, delivery of a liquid can be controlled more carefully, and there is no need to flood the entire channel with liquid in order to administer it, which can result in more economical use of the liquid.

At least part of the needle may be located within the probe tip channel, and may be affixed to a wall of the probe tip channel, for increased stability. The needle may be located in a needle guiding structure on a wall of the probe tip channel in order to ensure that during adjustment between the exposed and retracted positions, the longitudinal axis of the needle does not change its orientation relative to a longitudinal axis of the probe tip channel (i.e. an axis aligned with the axis of the coaxial transmission line). This allows greater control during adjustment of the needle, and may, for example, ensure that the needle is not scraped laterally across biological tissue during adjustment while the instrument is in use.

The largest diameter of the needle may be smaller than the smallest diameter of the aperture or of the probe tip channel. In this case, a plug may be provided to form a fluid tight seal between the needle and the wall of the probe tip channel.

Such a seal may allow injection of liquid to a target area from the needle when the liquid is in an exposed position, but prevent backflow of blood and other bodily fluids into the probe tip when the needle is in a retracted position. The plug may be formed from a non-rigid or resiliently deformable material which plugs the aperture, so that when the needle is in an exposed position, the plug exerts inward pressure on the outer surface of the needle, to form a fluid tight seal, and when the needle is in a retracted position, the resiliently deformable nature of the plug ensures that there is no hole present through the plug, i.e. seals shut the hole through which the needle can pass. The outermost end of the plug may lie flush with the surface of the probe tip, and may be shaped to form a continuous surface. Alternatively the plug may be located inside the probe tip channel, its outermost end spaced from the aperture. The plug may be made from silicone rubber.

The conducting element is preferably configured to act as a radiating monopole antenna. In order to emit a cylindrically isotropic microwave field, the probe tip may have cylindrical symmetry, to ensure that during use, the orientation of the microwave field is independent of rotation of the probe tip. This is advantageous because when inserted into the body, it may be difficult to manoeuvre the probe tip to the correct orientation. The probe may be domed, conical, or frustoconical in shape. These shapes may enable the probe tip to be used to apply pressure during treatment. When the probe tip has cylindrical symmetry, the longitudinal axis of the probe tip channel (i.e. an axis aligned with the axis of the coaxial transmission line) is preferably parallel to the axis of cylindrical symmetry of probe tip itself. More preferably, the axis of symmetry of the probe tip is the same as the longitudinal axis of the probe tip channel. The probe tip channel may be located in the centre of the probe tip, when viewed along the axis of symmetry of the probe tip. Alternative geometries for the probe tip include a cylindrical shape with a hemispherical distal end, and a ball shape. The probe tip may be elongate in shape, i.e. the length of the probe in the direction of the longitudinal axis may be longer than the maximum diameter of the probe tip. This will allow the probe to be aligned along a blood vessel in use, in order to cause coagulation which is distributed along the blood vessel, when operating in microwave radiation mode. Alternatively, the third dielectric material may be disc-shaped.

The probe tip channel may be aligned with the axis of the coaxial transmission line, at least in the neighbourhood of the interface between them.

The third dielectric material is preferably a low-loss, mechanically strong material. Here, "low loss" refers to a material through which microwaves may pass without a substantial loss of energy into the material. Preferable, the material has a dielectric loss tangent of less than 0.01, and more preferably less than 0.001. Furthermore, the third dielectric material is preferably sufficiently rigid that mechanical pressure may be applied to the site of a bleed during use of the instrument, without substantial deformation of the probe tip occurring. The third dielectric material may be one of: PEEK, PTFE or a ceramic, such as MACOR. The third dielectric material may be the same as, and may be continuous with the first dielectric material.

The inner conductor may be electrically connected to a conducting shell on the inner surface of the wall bounding the probe tip channel. Preferably, the conducting shell is a longitudinal extension of the inner conductor of the coaxial transmission line into the probe tip channel.

The conducting shell may act as a rod-shaped antenna which is able to transmit microwaves through the third dielectric material of the probe tip. When the inner surface of the probe tip channel is coated in a conducting shell in order to form a radiating monopole antenna, the needle is preferably insulated from said conducting shell, for example by a layer of insulating material which may cover the whole inner surface of the conducting shell, or alternatively, cover only the part where the needle contacts said inner surface.

The presence of the third dielectric material surrounding the conducting shell can improve energy delivery into tissue, e.g. by reducing the amount of reflected power, e.g. using an impedance matching transformer as discussed below.

Alternatively, the inner conductor may be electrically connected to a conducting shell on the surface of the wall bounding the probe tip channel, the conducting shell extending past the distal end of the probe tip channel and then curving or bending back on itself to form a conducting coating on an outer surface of the probe tip. The conducting coating may cover the whole of the probe tip, and may be electrically isolated from the outer conductor of the coaxial transmission line, i.e. not electrically connected to the outer conductor, in order to avoid a short circuit between the inner and outer conductors. The conducting coating may be electrically isolated from the outer conductor by means of a ring-shaped gap at the distal end of the probe tip, between the conducting coating and the outer conductor. Air in the gap may provide the required isolation. Alternatively, an insulating band may be provided between the two. In order to ensure a more uniform, continuous microwave field, when the conducting shell curves or bends back on itself as described above, the edge of the probe tip channel at its distal end may be a smooth, curved edge or a bevelled edge, rather than a sharply-angled edge.

The outer conductor of the coaxial transmission line may be grounded to form an unbalanced feed, or may be floating to form a balanced feed to the antenna, i.e. where the voltage on both the conductors is going up and down.

Preferably, in order to deliver microwave energy as efficiently as possible to a target area, the impedance of the radiating antenna structure is arranged to be well-matched to the impedance of the tissue of a target area at the frequency of the microwave field which is employed. In the case of matching the impedance to the impedance of blood, this ensures that the microwave field is able to cause efficient and easily-controlled coagulation. The impedance matching may be achieved by a quarter wave transformer located between the distal end of the coaxial transmission line and the probe tip. The length of this transformer may be approximately 5.5 mm if the third dielectric material is MACOR, or approximately 7 mm if the third dielectric material is PEEK. Additionally, a capacitance or inductance reactance matching stub may be used to match out the imaginary component of the impedance.

The liquid channel may be defined by the inner surface of the second dielectric material of the coaxial transmission line. The second dielectric material may represent a protective coating to prevent scratching of the conductors, e.g. when tools are passed through the hollow. The coaxial transmission line may be formed of an inner tube of dielectric material which forms the hollow second dielectric material. The hollow inner conductor may include a layer of conductive tape which is wrapped around said inner tube. The tape may include silver tape, copper tape or silver-plated copper tape. The first dielectric material may be formed of a dielectric tape which is wrapped around the inner conductor. The outer conductor may be formed of a layer of conductive tape which is similar to or identical to the conductive tape making up the inner conductor. A protective jacket made of a fourth dielectric material may also be provided on the outer surface of the outer conductor, wherein the fourth dielectric material may be the same as any one of the first, second and third dielectric materials.

Furthermore, the liquid channel may be provided as part of a lumen structure which is a separate entity from the inner conductor and/or the protective coating coated thereon, the lumen structure having an outer wall, the inner surface of which bounds the liquid channel. The lumen structure including the liquid channel may be provided inside the inner conductor. Accordingly the lumen structure may have a maximum outer diameter which is smaller than the minimum internal diameter of the inner conductor of the coaxial transmission line. In this way, the lumen structure can be placed inside the coaxial transmission line, for improved space-efficiency.

In addition to the liquid channel, the lumen structure may include a second channel for conveying additional tools such as a camera, materials, liquids or gases, and the like, to the probe tip and therefore the target area. The second channel may be larger than the liquid channel.

Where there is a second channel within the lumen structure, the probe tip may include a second probe tip channel, wherein the liquid channel and the second channel are in fluid communication respectively with the probe tip channel and the second probe tip channel, in order to prevent mixing/collision/entanglement of items being conveyed in different channels within the lumen structure. In particular, with the needle in the probe tip channel, only a single, liquid channel may be in fluid communication with the first end of the needle in order to allow liquid to be dispensed to the needle by flooding the liquid channel. If no other channel in the lumen structure is in fluid communication with the first end of the needle, there is minimal risk of the liquid entering a different channel. The needle-adjusting means may be located only in the liquid channel of the lumen structure, and the needle may be located only in the probe tip channel which is in fluid communication with the liquid channel.

The lumen structure may be an elongate, substantially cylindrically shaped structure configured to fit inside the inner conductor of the coaxial transmission line such that its outer surface is flush with the inner surface of the inner conductor. In the case where there is a protective coating on the inner surface of the inner conductor, the lumen structure may be flush with the inner surface of the protective coating. The liquid channel may be formed as an off-centre channel, defined by at least one of the outer wall of the lumen structure and a partition wall. The remainder of the lumen structure may then be used for conveying additional tools, materials, liquids or gases to the probe tip as described above.

The lumen structure is preferably made of a flexible material, such as PEBAX, nylon, polyimide, Kapton® or PTFE. This allows the lumen structure to bend along with bending of the elongate probe, and also to remain sufficiently rigid not to kink during bending.

Preferably, the liquid channel is arranged to convey adrenaline to the probe tip and/or the needle, which may be used for its vasoconstrictive properties. Alternatively the liquid channel may be arranged to convey liquids, e.g. saline, which restrict the blood vessels or clear the site so that energy can then be applied to stop a bleed.

The thicknesses of the inner and outer conductors making up the coaxial transmission line is preferably minimized in order to maximize the diameter of the hollow defined by the inner surface of the inner conductor. Furthermore, the thicknesses of the inner and outer conductor should be selected to ensure that the thickness of the first dielectric material is maximized, to ensure an acceptable level of loss at e.g. 5.8 GHz.

The coaxial transmission line may have an outside diameter of no more than 10 mm, and more preferably no more than 5 mm. Most preferably, the coaxial transmission line may have an outside diameter no more than 2.5 mm. Thus, the elongate probe may be sized to fit inside the instrument channel of a surgical scoping device, such as an endoscope, laparoscope or the like. The first dielectric material which separates the inner conductor from the outer conductor may be no more than 1 mm thick, and more preferably no more than 0.5 mm thick. The dielectric constant of the first dielectric material may be no more than 5, and more preferably no more than 3, and most preferably no more than 2.5. The first dielectric material may be polytetrafluoroethylene (PTFE).

Alternatively, a lower density material may be used for the first dielectric material, which has a higher air content than PTFE. For example, low-loss, low density PTFE may be used which may have a dielectric constant between 1.6 and 1.8. Alternatively, microporous PTFE having a dielectric constant between 1.3 and 1.5 may be used. This is possible due to the low voltages associated with the transmission of microwaves along the coaxial transmission line. In order to minimize the thickness of the first dielectric material, there is preferably only a single layer of material.

At least one of the inner or outer conductors may be made from silver. The thickness of the inner and outer conductors may be no more than 50 microns, and preferably no more than 25 microns, and most preferably no more than 10 microns. These thicknesses are sufficient for transmission of microwave energy along the coaxial transmission line but are as small as possible in order to maximize the size of the hollow defined by an inner surface of the hollow inner conductor.

The needle preferably has a diameter of no more than 1 mm, and more preferably no more than 0.5 mm, in order to fit through the liquid channel, and also to minimize the amount of space required for the needle.

According to another aspect of the invention, there is provided an electrosurgical apparatus having: an electrosurgical instrument as described above; a microwave feed structure configured to receive microwave EM energy from a microwave signal generator, and to convey the microwave EM energy to the electrosurgical instrument; a liquid feed structure configured to receive liquid from a liquid source, and to convey the liquid to the electrosurgical instrument.

The electrosurgical apparatus may include the microwave signal generator and/or the liquid source. The liquid source is preferably an adrenaline source.

The microwave feed structure may convey microwave EM energy to the coaxial transmission line of the electrosurgical instrument in a manner wherein access to the hollow feed is preserved. For example, the microwave feed structure may be incident upon the coaxial transmission line at approximately 90 degrees from the long axis of the coaxial transmission line, or at 45 degrees from the long axis of the coaxial transmission line.

The impedance of the microwave feed structure and the coaxial transmission line may be matched, for example by including a transformer arrangement electrically connected between the microwave feed structure and the proximal end of the coaxial transmission line of the electrosurgical instrument according to the first aspect of the invention (herein, "the electrosurgical instrument"). Matching impedance reduces power losses at the interface between the microwave feed structure and the proximal end of the coaxial transmission line of the electrosurgical instrument.

The electrosurgical apparatus may also include a handpiece, which can be held by a user in order to operate the electrosurgical apparatus. The handpiece may include attachment portions for connecting one or both of the microwave feed structure or the liquid feed structure. The attachment portions may be in the form of screw fittings. Having interfaces between the feed structures and the liquid channel/coaxial transmission line fixed inside a handpiece ensures that the relative orientation of the parts remains fixed, and less likely to be dislodged. Accordingly, the transformer arrangement may be located inside the handpiece, at the location of an interface between the microwave feed structure and the coaxial transmission line.

A section of intermediate coaxial transmission line, having an outer diameter which may be larger than the outer diameter of the coaxial transmission line of the electrosurgical instrument, may be located between the microwave feed structure and the coaxial transmission line of the electrosurgical instrument. A standard quarter wave transformer can be used at the interface of the microwave feed structure and the intermediate coaxial transmission line. The intermediate coaxial transmission line may include a tapering section, where it decreases in diameter to match the diameter of the coaxial transmission line of the electrosurgical instrument. The manner in which said line tapers may be optimized to minimize power losses or attenuation caused by impedance mismatch as a result of a change in diameter. A second quarter wave transformer may be present on the interface between the intermediate coaxial transmission line and the coaxial transmission line of the electrosurgical apparatus, in order to execute further impedance matching, and thus minimize power losses as a result of the signal switching between the microwave feed structure and the coaxial transmission line of the electrosurgical instrument.

The optional features set out above are applicable singly or in combination with any other features. Further optional features of the invention are set out below.

BRIEF DESCRIPTION OF THE DRAWINGS

Embodiments of the invention will now be described by way of example with reference to the accompanying drawings in which.

DETAILED DESCRIPTION OF THE DRAWINGS

Figure 1:
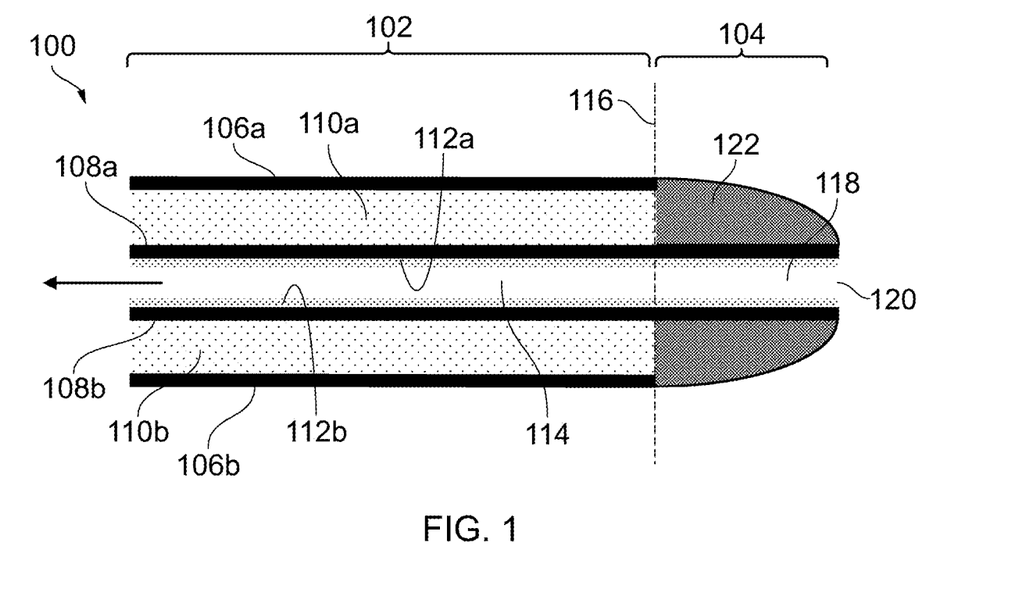
FIG. 1 is a schematic diagram showing a section lengthwise through part of an electrosurgical instrument.

FIG. 1 is a schematic diagram showing a section lengthwise through part of an electrosurgical instrument. The instrument 100 includes a coaxial transmission line 102 and a probe tip 104 which are joined at an interface 116. The coaxial transmission line 102 extends leftwards out of the drawing in the direction of the arrow towards a microwave feed structure and a liquid feed structure (not shown). The coaxial transmission line 102 is defined by an outer conductor 106a, 106b, and a hollow cylindrical inner conductor 108a, 108b, both formed of a conducting material such as silver. A dielectric material 110a, 110b separates the outer conductor 106a, 106b from the inner conductor 108a, 108b, both spatially and electrically. A protective coating 112a, 112b is located on the inner surface of the inner conductor 108a, 108b. The inner surface of the protective coating 112a, 112b defines a channel 114. The protective coating 112a, 112b is omitted from the remaining drawings, but it is noted that it is possible to include a protective coating in all of the embodiments of the present invention which are described below.

Probe tip 104 is connected to the coaxial transmission line 102 at the interface 116. The probe tip 104 has a third dielectric material 122, which is formed into a cylindrically-symmetrical dome shape, with a central probe tip channel 118 running along its axis of symmetry. The rightmost end of the probe tip channel 118 defines an aperture 120. Both the inner conductor 108a, 108b and the protective coating 112a, 112b extend continuously past the interface 116 to form the cylindrical wall of the probe tip channel 118. As a result, in the present embodiment, the probe tip channel 118 is continuous with, and has the same diameter as the channel 114 to enable a tool to be easily passed through the channel 114 into the probe tip channel 118.

In operation, the coaxial transmission line is connected to receive a signal from a microwave signal generator (not shown) and the inner conductor 108a, 108b and the outer conductor 106a, 106b act as a waveguide to convey the microwave energy along the coaxial transmission line 102.

The cylindrical portion of the inner conductor 108a acts as a monopolar radiating antenna, and is coupled to receive the microwave energy from the coaxial transmission line 102 and thereby emits a microwave field, via the dielectric material 122, to the surroundings.

Figure 2:
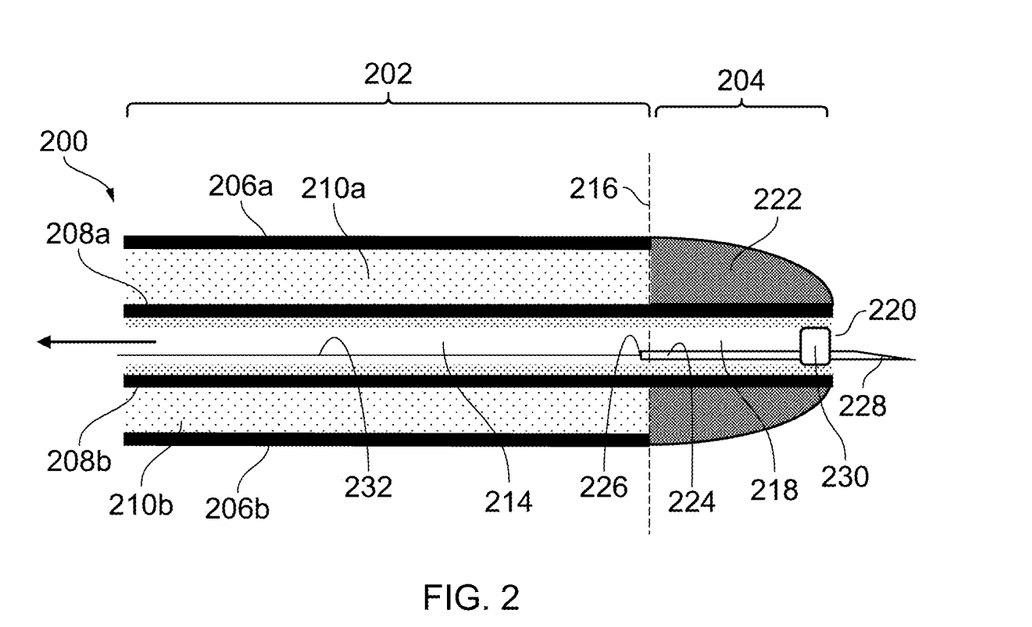
FIG. 2 is a schematic diagram showing a section lengthwise through part of an electrosurgical instrument according to a first embodiment of the present invention, showing a hollow needle in an exposed position.
Figure 3:
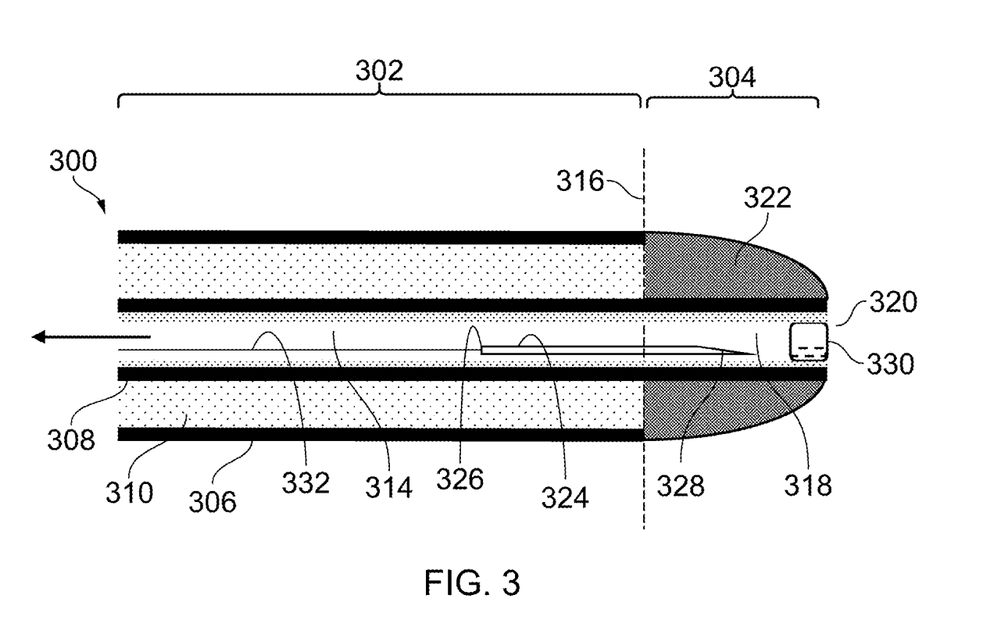
FIG. 3 is a schematic diagram showing a section lengthwise through part of an electrosurgical instrument according to the first embodiment of the present invention, showing a hollow needle in a retracted position.

FIG. 2 and FIG. 3 are schematic diagrams each showing a section lengthwise through part of an electrosurgical instrument according to an embodiment of the present invention. Description here is not repeated for those features which have already been described. Features labelled with the same second and third digit as the previous drawing are considered equivalent. In the embodiment depicted in FIG. 2, a hypodermic needle 224 is located inside the central channel of the probe 200 which is formed by the channel 214 and the probe tip channel 218. Needle 224 has a first end 226 and a second end 228. A guide wire 232 made of a rigid metal is attached to the first end 226 of the needle 224. The guide wire 232 is used to move the needle 224 left and right, in the view of FIG. 2, i.e. forwards and backwards along the probe tip channel 218. A plug 230 is located in the aperture 220 of the probe tip channel 218. The plug 230 is formed of a rubber-like material which is able to form a tight seal with the wall of the probe tip channel 218, formed by inner conductor 108a, 108b. Plug 230 has an aperture running through it, through which needle 224 can be passed. When the needle 224 passes through plug 230, and the second end 228 of the needle 224 protrudes from the plug 230, exposed to the surroundings, the needle 224 is in an exposed position. In this position, when a liquid is fed to the first end 226 of the needle 224, it can exit through the second end 228 of the needle to the surrounding area, for treatment or otherwise.

The guide wire 232 can be used to draw the needle 224 from the position depicted in FIG. 2, to the position shown in FIG. 3.

In FIG. 3, the needle 324 is withdrawn such that the second end of the needle is situated inside the probe tip channel 318, and is no longer exposed to the surrounding area. This is a retracted position. When the needle 324 is in this position, the resiliently deformable nature of the plug 330 ensures that it seals itself, preventing liquid inside the probe tip channel 318 from escaping to the surroundings, and preventing liquid or other matter from the surroundings from entering the probe tip channel 318, and contaminating its contents. From the retracted positon of needle 324 shown in FIG. 3, the guide wire may be used to push the needle back through the plug 330 to return it to the exposed position depicted in FIG. 2.

Figure 4:
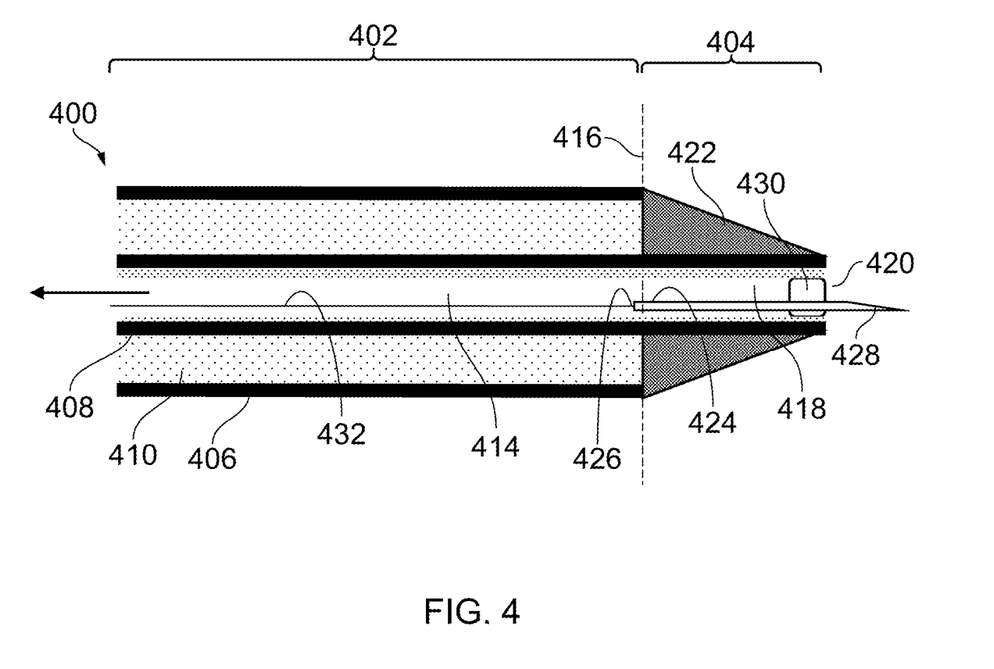
FIG. 4 is a schematic diagram showing a section lengthwise through part of an electrosurgical instrument according to a second embodiment of the present invention.
Figure 5:
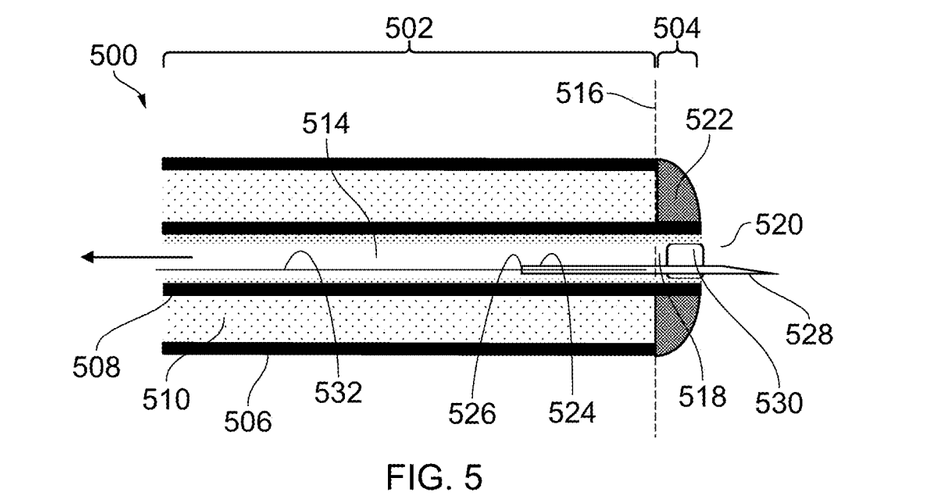
FIG. 5 is a schematic diagram showing a section lengthwise through part of an electrosurgical instrument according to a third embodiment of the present invention.
Figure 6:
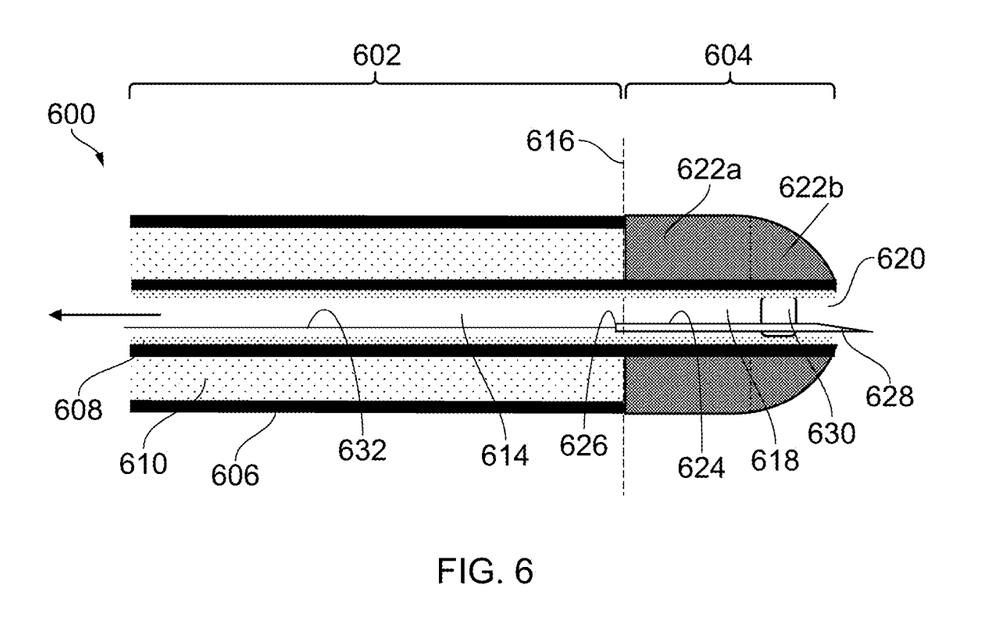
FIG. 6 is a schematic diagram showing a section lengthwise through part of an electrosurgical instrument according to a fourth embodiment of the present invention.

FIGS. 4, 5 and 6 show alternative embodiments of the present invention having different probe tip geometries. Probe tip 404 in FIG. 4 is conically shaped. In similar embodiments, the edge of the cone which surrounds the aperture 520 may be curved or bevelled.

Probe tip 504 of FIG. 5 is dome-shaped, similar to the embodiments shown in FIGS. 1 to 3, but with a shallower dome of dielectric material 522, and therefore a shorter probe tip channel 518.

In the embodiment shown in FIG. 6, the probe tip 604 is formed of a cylindrical section of dielectric material 622a, and a hemispherical section 622b. The two sections are continuous, and integrally formed. The dotted line in the drawing merely delineates the cylindrical part 622a from the hemispherical part 622b, and does not represent a discontinuity or a joint.

Figure 7:
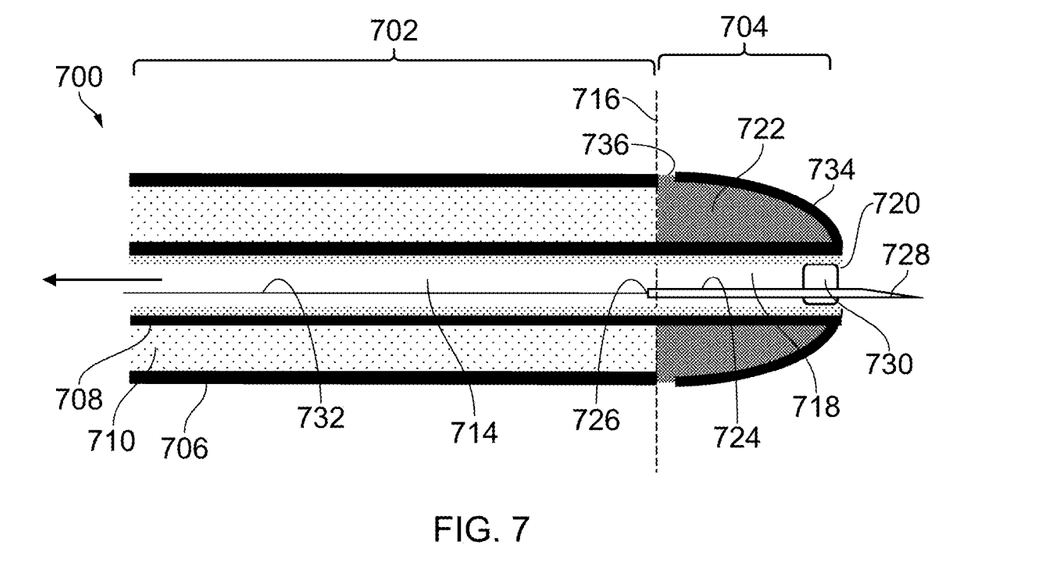
FIG. 7 is a schematic diagram showing a section lengthwise through part of an electrosurgical instrument according to a fifth embodiment of the present invention.
Figure 8:
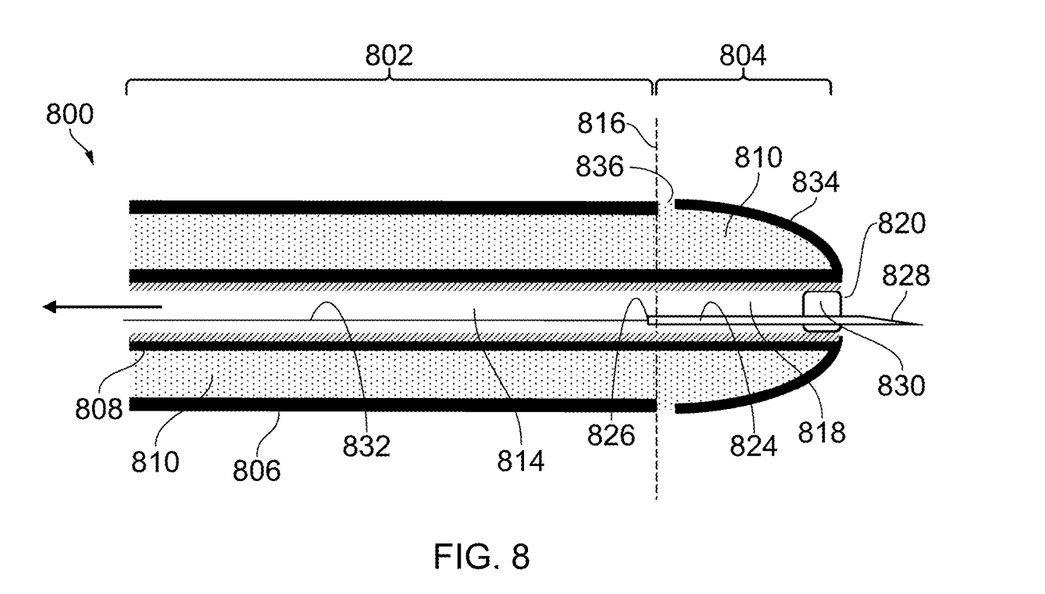
FIG. 8 is a schematic diagram showing a section lengthwise through part of an electrosurgical instrument according to a sixth embodiment of the present invention.

FIG. 7 is a schematic diagram showing a section lengthwise through part of an electrosurgical instrument according to another embodiment of the present invention. In the electrosurgical instrument 700 shown in FIG. 7, the antenna structure of the probe tip 704 differs from those described in previous embodiments. The inner conductor 708 which forms the wall of probe tip channel 718, rather than terminating at the aperture 720, as in previous embodiments, extends out of the aperture, and folds back round to cover the outer surface of dielectric material 722. The portion 734 of the conducting material which covers the dielectric material 722 is electrically isolated from the outer conductor 706a, 706b. For example, a space 736 can be located all the way around the circumference of the probe tip. FIG. 8 shows an embodiment similar to FIG. 7. The two differ only in that in the embodiment shown in FIG. 8, the dielectric material 810a, 810b of the coaxial transmission line is continuous with the dielectric material 822 in the probe tip 804. It is noted that the same dielectric materials may be used for the coaxial transmission line and the probe tip in all of the foregoing embodiments.

Figure 9:
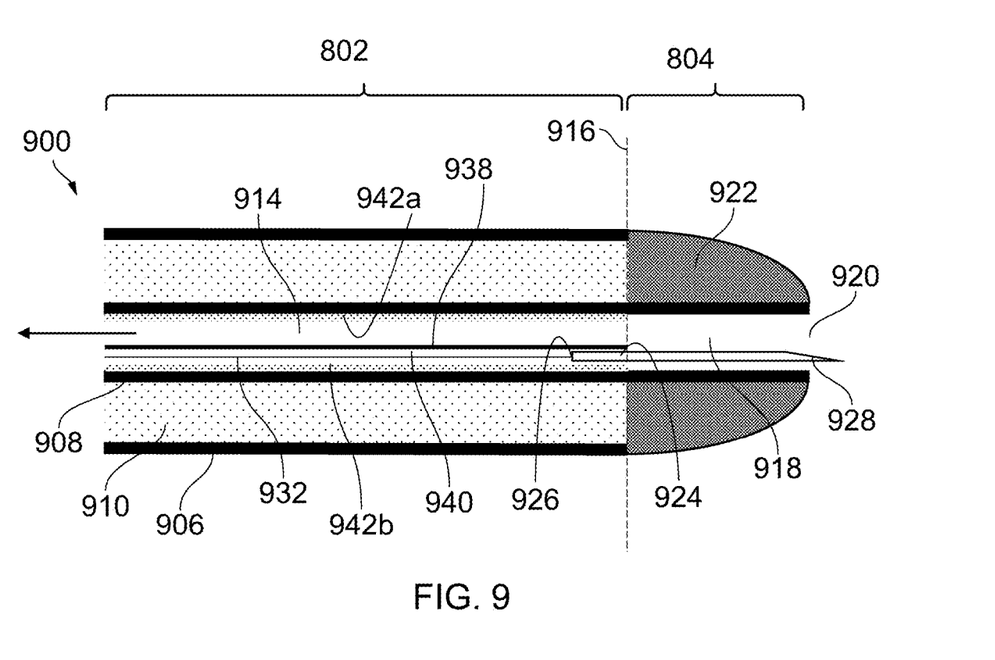
FIG. 9 is a schematic diagram showing a section lengthwise through part of an electrosurgical instrument according to an seventh embodiment of the present invention.
Figure 10:
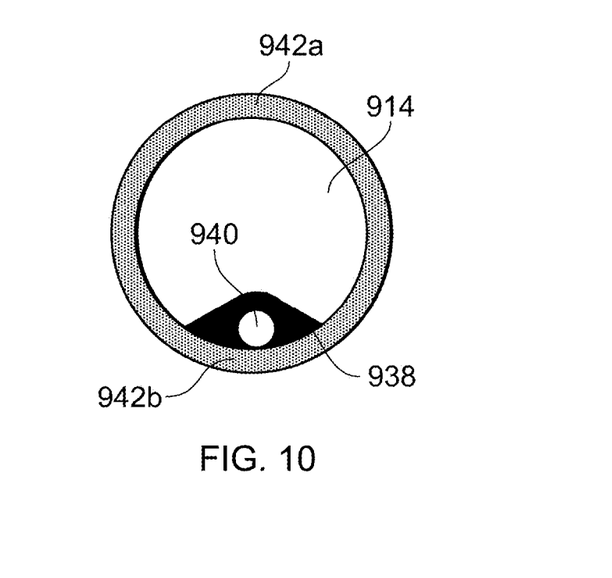
FIG. 10 is a schematic diagram showing a transverse cross section through part of an electrosurgical instrument according to an seventh embodiment of the present invention.

FIG. 9 is a schematic diagram showing a section lengthwise through part of an electrosurgical instrument according to another embodiment of the present invention. Here, the structure of the channel 914 which is located in the hollow of the coaxial transmission line defined by the inner conductor 908a, 908b, is different. In the channel defined by the inner conductors 908a, 908b is a lumen structure, a typical cross-section of which is shown in FIG. 10. The lumen structure has a cylindrical outer wall 942a, 942b and a partition wall 938, which define two channels, the main channel 914 (as in all other embodiments) and a smaller needle channel 940. The needle channel 940 is smaller in diameter than the main channel 914, and is not much wider than the needle 924 itself, in other embodiments, the needle channel 940 may be shaped to be the same diameter as the needle. In this embodiment, the needle channel 940 may be flooded with liquid in order to supply the first end 926 of the needle with liquid to administer to the surroundings. No plug is required in the present embodiment because the needle channel 940 is isolated from the main channel 914. The main channel 914 can be used to convey separate items to the surroundings, if necessary.

Figure 11:
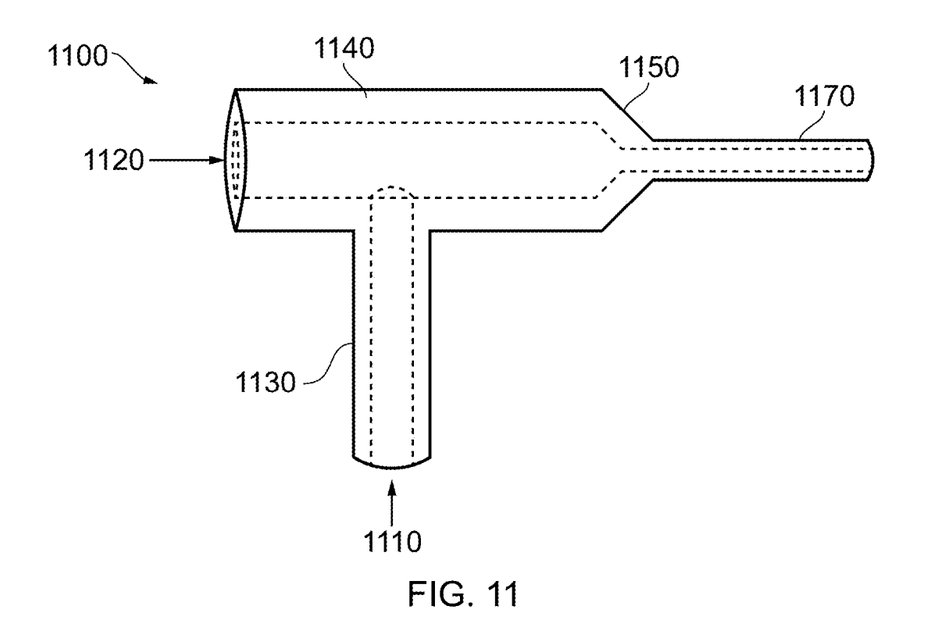
FIG. 11 is a schematic diagram of a handpiece which may be used in an electrosurgical apparatus which includes electrosurgical instruments according to any of the first to seventh embodiments of the present invention.
Figure 12:
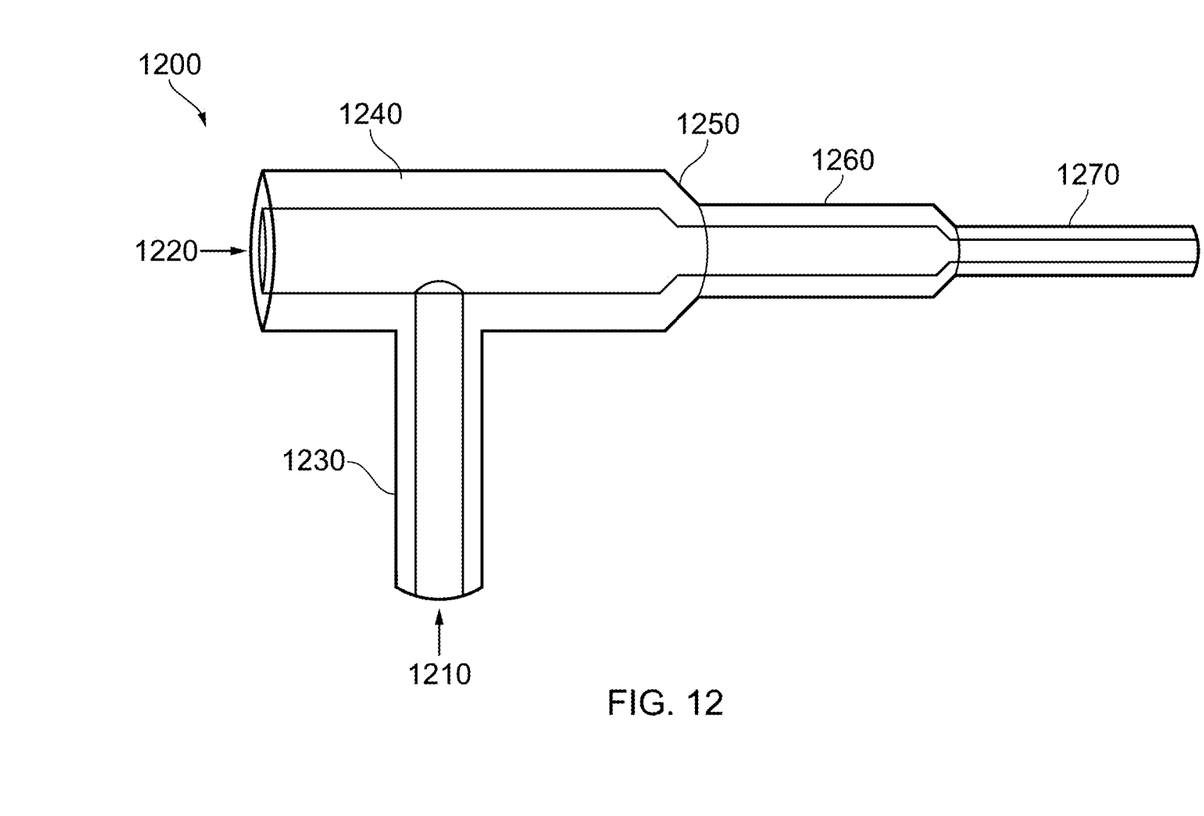
FIG. 12 is a schematic diagram of an alternative handpiece which may be used in an electrosurgical apparatus which includes electrosurgical instruments according to any of the first to seventh embodiments of the present invention.

FIGS. 11 and 12 are schematic diagrams of connectors 1100 and 1200 which may be used in handheld controllers (also referred to herein as "handpieces") to operate the present invention, the details of the cables shown in these drawings are not shown, but in particular, the cable sections 1170, 1270 correspond to the elongate probe section of any one of FIGS. 1 to 9, and the large coaxial transmission line section is a similar structure, only having a larger diameter.

In particular these diagrams illustrate the mechanisms by which impedance-matching between a microwave signal generator and the coaxial transmission line as shown in FIGS. 1 to 9. In FIG. 10, the handpiece 1100 is connected at input 1120 to a liquid feed structure (not shown) which delivers a liquid such as adrenaline from a liquid source (also not shown) to the handpiece 1100. The input 1120 feeds directly into a hollow channel at the centre of the large coaxial transmission line section 1140, for transmission into the smaller diameter cable 1170, which corresponds to the coaxial transmission line e.g. 102 as shown in the foregoing drawings.

Microwave signals generated by a microwave signal generator (not shown) are transmitted by a microwave feed structure (also not shown) to input 1110. From input 1110, the microwave signals pass through quarter-wave transformer 1130 to the inner and outer conductors of the large coaxial transmission line section 1140, the quarter wave transformer 1130 acting to match the impedance of the large coaxial transmission line to the input impedance of the microwave feed structure.

A matching impedance for the quarter wave transformer is calculated using the following formula:

$$Z_{matching} = \sqrt{Z_1 Z_2}$$

Where $Z_1$ and $Z_2$ are the input and output impedances.

The impedance of the large coaxial transmission line section 1170 is an intermediate value between the impedance of the microwave feed structure and the cable 1140. The length of the large coaxial transmission line section, from the point where the microwaves enter, to the beginning of tapering section 1150 is an integer multiple of $\lambda/2$ where $\lambda$ is the wavelength of the microwaves generated by the microwave signal generator, which allows the large coaxial transmission line section to be "invisible" and improve matching with cable 1140. Microwave signals are then conveyed through a 45° tapering section 1150, to the smaller diameter cable 1170, in order to ensure than an abrupt step in the cable is not present, which would lead to undesirable power loss due to reflections at the interface. From the tapering section 1150, the microwave signals are conveyed to the cable 1170.

In an alternative embodiment, also schematically represented by FIG. 11, the large coaxial transmission line section 1140 has a geometry which ensures that it has the same impedance as the cable 1170. In this way, no further impedance-matching devices are required. The appropriate geometry can be ascertained from the following equation:

$$\frac{b}{a} = \exp\left(\frac{Z_0 \sqrt{\epsilon_r}}{60}\right)$$

where b/a represents the ratio of inner diameter of the outer conductor the outer diameter of the inner conductor, $Z_0$ is the impedance of the transformer and $\epsilon_r$ is the dielectric constant of the dielectric material.

FIG. 12 shows an alternative handpiece. In FIG. 12, as with FIG. 11, the handpiece 1200 is connected at an input 1220 to a liquid feed structure (not shown) which delivers a liquid such as adrenaline from a liquid source (also not shown) to the handpiece 1200. The input 1220 feeds directly into a hollow channel at the centre of the large coaxial transmission line section 1240, for transmission into the smaller diameter cable 1170, which corresponds to the coaxial transmission line e.g. 102 as shown in the foregoing drawings.

Microwave signals generated by a microwave signal generator (not shown) are transmitted by a microwave feed structure (also not shown) to input 1210. From input 1210, the microwave signals pass through quarter-wave transformer 1230 to the inner and outer conductors of the large coaxial transmission line section 1240, the quarter wave transformer 1230 acting to match the impedance of the large coaxial transmission line to the input impedance of the microwave feed structure. The signals then pass through a first 45° tapering structure 1250, before passing through a second quarter wave transformer 1260, from which the signals are incident upon cable 1270. In this embodiment the inclusion of two quarter wave transformers 1230 and 1260 allows the large section of coaxial transmission line to have any geometry as the quarter wave transformers 1230, 1260 ensure impedance matching between the microwave feed structure and the cable 1270.

Figure 13:
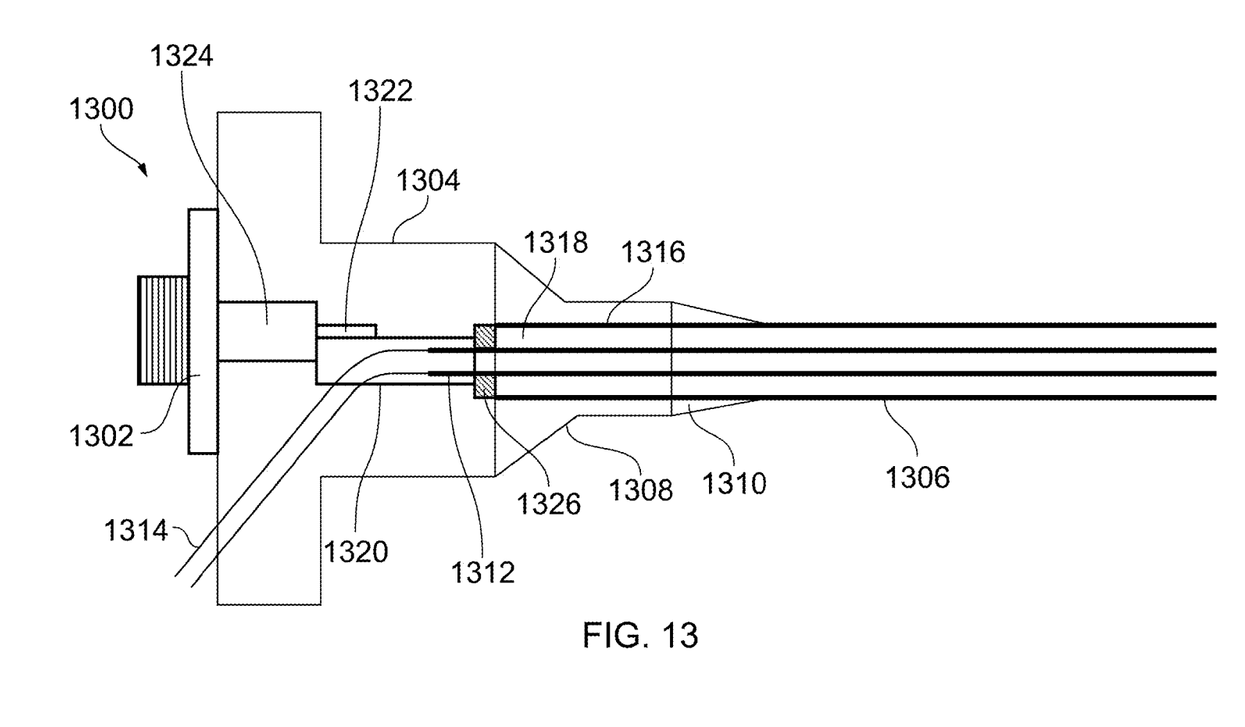
FIG. 13 is a schematic cross-sectional view through a proximal connector for a coaxial transmission line that is suitable for use with the invention.

FIG. 13 shows a proximal connecter 1300 that can be used to feed microwave energy and liquid into the electrosurgical instrument discussed above. The proximal connector 1300 comprises a standard coaxial connector 1302, such as an SMA connector, mounted at the proximal end of an outer body 1304. The coaxial connector 1302 is arranged to receive a conventional coaxial cable (not shown) which can convey microwave energy from a microwave signal generator (not shown). The outer body 1304 is arranged to receive at its distal end a proximal portion of the hollow coaxial transmission line 1306 that formed part of the invention discussed above.

Within the outer body 1304, the inner conductor 1312 and hollow inner dielectric tube 1314 extend away from a proximal termination of the outer conductor 1316 and the first dielectric material 1318 of the coaxial transmission line. The inner conductor 1312 and hollow inner dielectric tube 1314 are received in an inner body 1320 of the proximal connector 1300, which in this example is a short conductive tube. The inner conductor 1312 is in electrical contact with and terminates within the inner body 1320. The hollow inner dielectric tube 1314 extends through the inner body 1320 and exits through an aperture formed in a side surface thereof.

The inner body 1320 is electrically connected (e.g. by soldering) to a distal inner conductive element 1322 of the coaxial connector 1302. In this way, the inner conductor 1312 of the coaxial transmission line 1306 is connected to the inner conductor of the coaxial cable that delivers the microwave energy.

The outer body 1304 has a distal ferrule 1308 which is electrically connected (e.g. via solder 1310) to the outer conductor 1316 of the coaxial transmission line 1306. The outer body 1304 and its distal ferrule 1308 are made from conductive material and are electrically connected via the coaxial connector 1302 to the outer conductor of the coaxial cable that delivers the microwave energy.

An insulating sleeve 1324 isolates the inner conducive element 1322 from the outer body 1304.

The hollow inner dielectric tube 1314 extends through the outer body 1304 to a liquid source (not shown). A dielectric spacer 1326 (e.g. made from PTFE) separates (and ensures electrical isolation between) the inner body 1320 and the proximal end of the outer conductor 1316.

The dimensions of the proximal connector 1300 shown in FIG. 13 may be selected so that it acts as a quarter wave impedance transformer between the coaxial cable and the coaxial transmission line 1306.

Using the dimensions and materials discussed herein, the coaxial transmission line 1306 may have a characteristic impedance of approximately 14Ω. A typical characteristic impedance of a standard coaxial cable is 50Ω. The diameters of the inner body 1320 and outer body 1304 in the proximal connector can be set to provide the required impedance for a length L equal to one quarter wavelength. The inner body 1320 and outer body 1304 in this example form an air-filled coaxial line ($\varepsilon_r$=1) with the following characteristics: $Z_0$=26.5Ω, a=4 mm, b=6.1 mm and L=12.9 mm, where a and b correspond to the outer diameter of the inner conductor and the inner diameter of the outer conductor respectively.

Providing a passage for the hollow inner dielectric tube 1314 that extends at an angle (e.g. 45°) to the longitudinal axis of the coaxial transmission line 1306 limits any interference with the operation of the transformer itself. It was found that due to the small diameter of the tube, even when passed directly through the conductors, a good match was still found between microwave source and cable.

Figure 14:
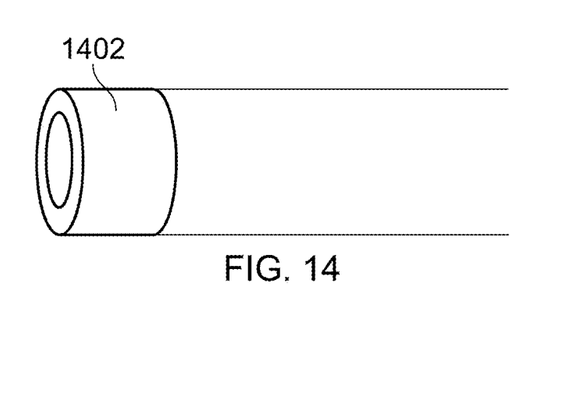
FIG. 14 is schematic perspective view of a distal tip of an electrosurgical instrument that is an embodiment of the invention.

FIG. 14 show an exterior view of an electrosurgical instrument that is another embodiment of the invention. This embodiment is identical to FIG. 1 except that the probe tip comprises an annular tip body 1402 made from Macor, which is a machinable glass-ceramic developed by Corning Inc. Macor was chosen for this prototype due to its good thermal and electrical insulation across a range of frequencies and ease of machining.

Figure 15:
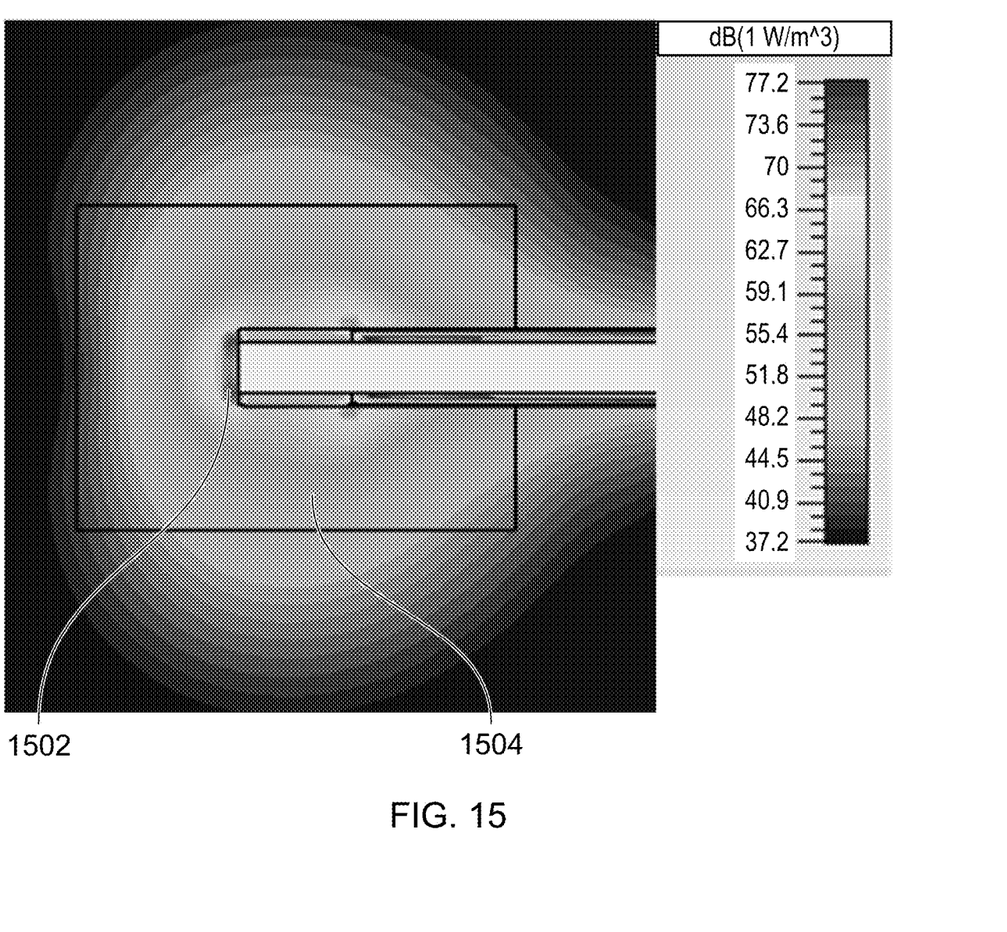
FIG. 15 is a simulation showing microwave field strength emitted by the instrument shown in FIG. 14.

A series of tips having the structure shown in FIG. 14 were simulated when radiating into liver. FIG. 15 shows the power density distribution of the chosen tip design. At the distal end of the tip there is a region 1502 having a maximum power density of 74.43 dBm/m$^3$. Assuming a specific heat density of 3.49 kJkg$^{-1}$K$^{-1}$ and a tissue density of 1060 kg/m$^3$ it can be calculated that the required energy to achieve coagulation in 1 cm$^3$ of tissue is approximately 3.7 J. To achieve coagulation the tissue needs to be heated by approximately 23° C., giving a total energy requirement of around 85.1 J. As per simulation of the current design of the radiative tip this can be achieved in 0.3 s in region 1502 and in 8.5 s in region 1504.

Figure 16:
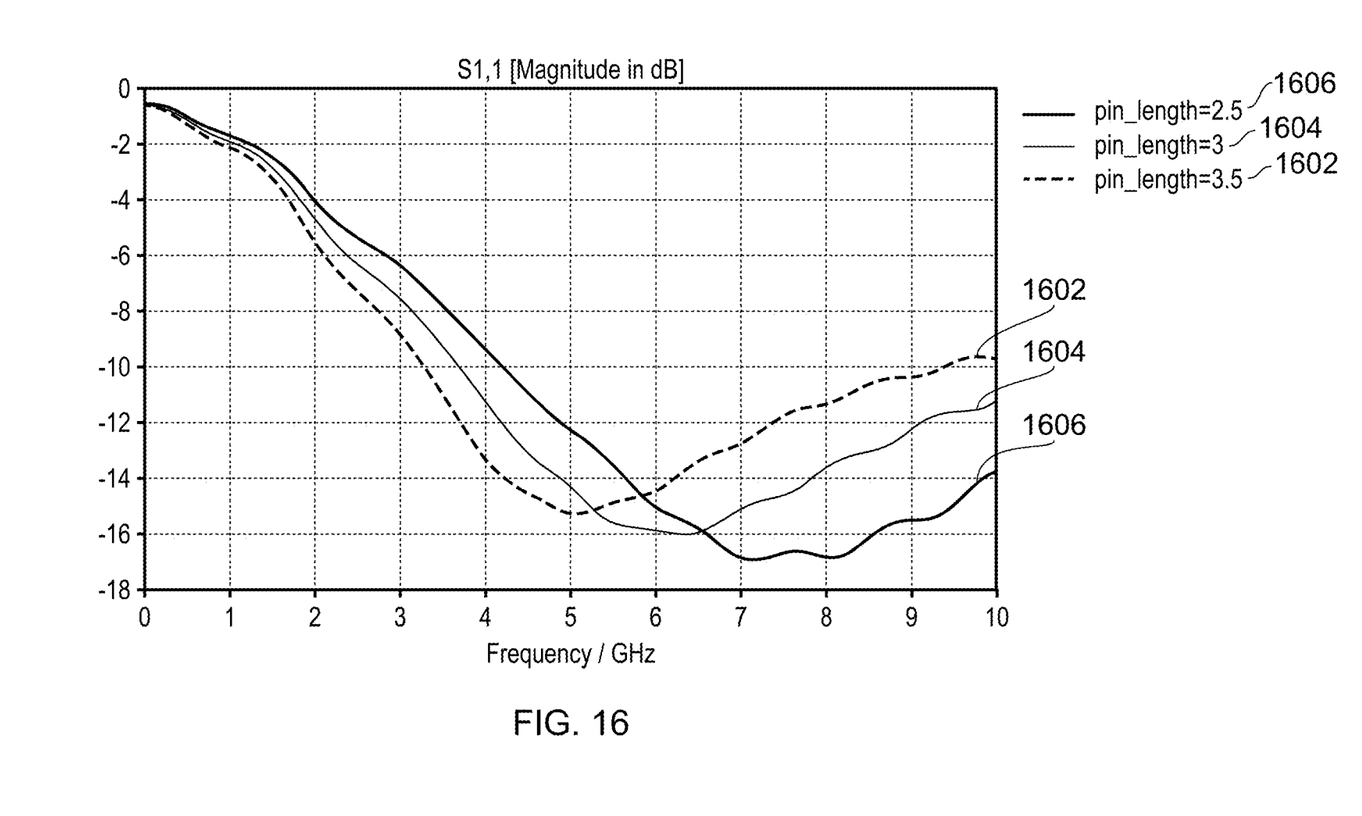
FIG. 16 is a graph showing return loss for the instrument shown in FIG. 14 when provided with different tip lengths.

FIG. 16 shows the return loss measurements for three different tip lengths. Line 1602 corresponds to a tip length of 3.5 mm. Line 1604 corresponds to a tip length of 3 mm. Line 1606 corresponds to a tip length of 2.5 mm. It can be seen that simulated results suggest that a 3 mm tip provides a better match into tissue giving a return loss of approximately −16 dB at 5.8 GHz.

The invention claimed is:
1. An electrosurgical instrument comprising:
an elongate probe having:
 a coaxial transmission line for conveying microwave electromagnetic (EM) energy,
 a probe tip connected at a distal end of the coaxial transmission line for receiving the microwave energy, and
 a liquid channel located inside the coaxial transmission line for conveying liquid through the elongate probe to the probe tip,
wherein the coaxial transmission line comprises:
 a hollow inner conductor,
 an outer conductor,
 a first dielectric material separating the inner conductor from the outer conductor, and
 a hollow second dielectric material on an inner surface of the hollow inner conductor, the liquid channel located inside the hollow second dielectric material;
wherein the probe tip has a probe tip channel running therethrough, the probe tip channel terminating in an aperture at a distal end of the probe tip channel,
wherein the probe tip includes a conductive element coupled to receive the microwave energy from the coaxial transmission line, the conductive element forming a radiating antenna structure for emitting a microwave EM field outwardly from the probe tip,
wherein the instrument further comprises a hollow needle located inside the liquid channel, wherein a first end of the needle is in fluid communication with the liquid channel and a second end of the needle is arranged to deliver the liquid from the liquid channel through the aperture of the probe tip channel to a target area, and wherein the needle is adjustable between:
a retracted position for use during emission of the microwave EM field by the radiating antenna structure, in which the second end of the needle is located inside the probe tip channel or the liquid channel, and
an exposed position, in which the second end of the needle is located outside the probe tip channel, past the aperture at the distal end of the probe tip channel.

2. The electrosurgical instrument according to claim 1, wherein the microwave EM energy has a frequency no less than 400 MHz and no more than 100 GHz.

3. The electrosurgical instrument according to claim 1, wherein the probe tip comprises a continuation of the hollow second dielectric material beyond the distal end of the coaxial transmission line.

4. The electrosurgical instrument according to claim 1, wherein the conductive element is a conducting shell disposed on an inner surface of the probe tip channel.

5. The electrosurgical instrument according to claim 4, wherein the hollow inner conductor extends beyond the distal end of the coaxial transmission line into the probe tip to form the conducting shell.

6. The electrosurgical instrument according to claim 4, wherein the probe tip comprises a tip body having the probe tip channel running therethrough, the tip body being formed from a third dielectric material and being connected to the distal end of the coaxial transmission line.

7. The electrosurgical instrument according to claim 6, wherein a conductive coating is formed on an outer surface of the probe tip, and wherein the conducting shell is electrically connected to the conductive coating through the aperture.

8. The electrosurgical instrument according to claim 7, wherein the conductive coating is electrically isolated from the outer conductor of the coaxial transmission line.

9. The electrosurgical instrument according to claim 1, wherein the probe tip is cylindrically symmetrical about an axis of symmetry that is in line with a longitudinal axis of the coaxial transmission line.

10. The electrosurgical instrument according to claim 1 including a guide wire mounted within the liquid channel and connected to the needle, the guide wire being attached to an actuator at a proximal end of the liquid channel, the actuator being operable to move the guide wire axially within the liquid channel to switch the needle between the retracted position and the exposed position.

11. The electrosurgical instrument according to claim 1, wherein a largest diameter of the needle is smaller than a smallest diameter of the probe tip channel, and further including a plug in the probe tip channel through which the needle can pass, the plug forming a fluid tight seal with an inner surface of the probe tip channel.

12. The electrosurgical instrument according to claim 11, wherein the plug is made of a resiliently deformable material.

13. The electrosurgical instrument according to claim 1, wherein a multi-lumen structure is provided within the hollow second dielectric material.

14. The electrosurgical instrument according to claim 13, wherein the multi-lumen structure includes the liquid channel and a second channel, separated from each other by a partition wall.

15. The electrosurgical instrument according to claim 14, wherein the probe tip has a second probe tip channel running therethrough, the second probe tip channel being in fluid communication with the second channel.

16. The electrosurgical instrument according to claim 1, wherein an outer diameter of the coaxial transmission line is equal to or less than 5 mm.

17. The electrosurgical instrument according to claim 1, wherein the first dielectric material has a thickness equal to or less than 1 mm.

18. The electrosurgical instrument according to claim 1, wherein:
the hollow needle is insulated from the conductive element and the radiating antenna structure.

19. An electrosurgical apparatus having:
the electrosurgical instrument according to claim 1;
a microwave feed structure configured to receive microwave EM energy from a microwave signal generator, and to convey the microwave EM energy to the electrosurgical instrument; and
a liquid feed structure configured to receive liquid from a liquid source, and to convey the liquid to the electrosurgical instrument.

20. The electrosurgical apparatus according to claim 19, wherein the liquid source is an adrenaline source.

21. The electrosurgical apparatus according to claim 19 further comprising an intermediate coaxial transmission line connected at a first end to the microwave feed structure, and at a second end to the coaxial transmission line of the electrosurgical instrument.

22. The electrosurgical apparatus according to claim 21, wherein a quarter-wave transformer is connected at:
an interface between the microwave feed structure and the intermediate coaxial transmission line, or
an interface between the intermediate coaxial transmission line and the coaxial transmission line of the electrosurgical instrument.

23. The electrosurgical apparatus according to claim 21 wherein dimensions of the intermediate coaxial transmission line selected are selected either:
to match an impedance between the microwave feed structure and the coaxial transmission line of the electrosurgical instrument, or
to be an integer multiple of half-wavelengths of a microwave signal being transmitted by the microwave feed structure.

* * * * *